(12) United States Patent
Fangrow, Jr.

(10) Patent No.: US 7,297,138 B2
(45) Date of Patent: *Nov. 20, 2007

(54) INFUSION SET

(75) Inventor: Thomas F. Fangrow, Jr., Mission Viejo, CA (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/417,655

(22) Filed: May 3, 2006

(65) Prior Publication Data

US 2006/0270992 A1 Nov. 30, 2006

Related U.S. Application Data

(63) Continuation of application No. 10/715,985, filed on Nov. 18, 2003.

(51) Int. Cl.
*A61M 5/178* (2006.01)
(52) U.S. Cl. .............................. 604/167.02; 604/164.01
(58) Field of Classification Search ........... 604/164.01, 604/164.04, 167.01–167.02, 180, 890.1, 604/288.02, 533
See application file for complete search history.

(56) References Cited

U.S. PATENT DOCUMENTS

| 3,861,972 A | 1/1975 | Glover et al. |
| 3,964,470 A | 6/1976 | Trombley |
| 4,235,234 A | 11/1980 | Whitney et al. |
| 4,352,354 A | 10/1982 | Ujihara |
| 4,352,358 A | 10/1982 | Angelchik |
| 4,362,156 A | 12/1982 | Feller, Jr. et al. |

(Continued)

FOREIGN PATENT DOCUMENTS

EP 0256694 2/1988

(Continued)

OTHER PUBLICATIONS

International Search Report for PCT/US2004/037883 dated Mar. 15, 2005.

(Continued)

*Primary Examiner*—Kevin C. Sirmons
*Assistant Examiner*—Andrew Gilbert
(74) *Attorney, Agent, or Firm*—Knobbe Martens Olson & Bear, LLP.

(57) ABSTRACT

An infusion set comprises a base member (60), an introducer cap (64), and an infusion cap (54). The base member (60) preferably comprises a soft cannula (52) extending from a lower side (118) of the base member (60), and a port (62) on an upper side (92) thereof. The port (62) is configured to be in fluid communication with the cannula (52). The port (62) also comprises a septum (130) adapted to seal the port (62) against unwanted fluid flow. The introducer cap (64) is adapted to be mounted to the base member (60) and has a needle (66) adapted to extend through the septum (130) and said soft cannula (52) in an assembled position. The infusion cap (54) comprises a lumen (160) adapted to receive an elongate flexible tube (162). The infusion cap (54) also comprises a hard cannula (170) adapted to be inserted through the septum (130) and to place said soft cannula (52) in fluid communication with said lumen (160).

16 Claims, 11 Drawing Sheets

U.S. PATENT DOCUMENTS

| | | | |
|---|---|---|---|
| 4,531,937 A | 7/1985 | Yates | |
| 4,576,211 A | 3/1986 | Valentini et al. | |
| 4,619,247 A | 10/1986 | Inoue | |
| 4,619,643 A | 10/1986 | Bai | |
| 4,664,656 A | 5/1987 | Taddei | |
| 4,713,057 A | 12/1987 | Huttner et al. | |
| 4,723,947 A | 2/1988 | Konopka | |
| 4,752,292 A | 6/1988 | Lopez et al. | |
| 4,755,173 A | 7/1988 | Konopka et al. | |
| 4,863,432 A | 9/1989 | Kvalo | |
| 4,944,728 A | 7/1990 | Carrell et al. | |
| 4,966,588 A | 10/1990 | Rayman et al. | |
| 5,078,689 A | 1/1992 | Keller | |
| 5,084,015 A | 1/1992 | Moriuchi | |
| 5,098,397 A * | 3/1992 | Svensson et al. | 604/175 |
| 5,176,662 A | 1/1993 | Bartholomew et al. | |
| 5,186,712 A | 2/1993 | Kelso et al. | |
| 5,257,980 A | 11/1993 | Van Antwerp et al. | |
| 5,267,967 A | 12/1993 | Schneider | |
| 5,338,314 A | 8/1994 | Ryan | |
| 5,344,414 A | 9/1994 | Lopez et al. | |
| 5,423,775 A | 6/1995 | Cannon | |
| 5,487,728 A | 1/1996 | Vaillancourt | |
| 5,501,676 A | 3/1996 | Niedospial et al. | |
| 5,507,733 A | 4/1996 | Larkin et al. | |
| 5,514,117 A | 5/1996 | Lynn | |
| 5,522,803 A | 6/1996 | Teissen-Simony | |
| 5,545,143 A | 8/1996 | Fischell | |
| 5,545,152 A | 8/1996 | Funderburk et al. | |
| 5,549,583 A | 8/1996 | Sanford et al. | |
| 5,562,617 A | 10/1996 | Finch et al. | |
| 5,584,813 A | 12/1996 | Livingston et al. | |
| 5,591,188 A | 1/1997 | Waisman | |
| D380,262 S | 6/1997 | Van Funderburk et al. | |
| 5,637,098 A | 6/1997 | Bierman | |
| 5,665,071 A | 9/1997 | Wyrick | |
| 5,685,866 A | 11/1997 | Lopez | |
| 5,702,371 A | 12/1997 | Bierman | |
| 5,718,682 A | 2/1998 | Tucker | |
| 5,722,959 A | 3/1998 | Bierman | |
| 5,776,116 A | 7/1998 | Lopez et al. | |
| 5,810,781 A | 9/1998 | Bierman | |
| 5,851,197 A | 12/1998 | Marano et al. | |
| 5,858,005 A | 1/1999 | Kriesel | |
| 5,954,643 A | 9/1999 | Van Antwerp et al. | |
| 5,954,708 A | 9/1999 | Lopez et al. | |
| 5,968,001 A | 10/1999 | Freeman | |
| 5,968,011 A | 10/1999 | Larsen et al. | |
| 5,971,950 A | 10/1999 | Lopez et al. | |
| 5,980,506 A | 11/1999 | Mathiasen | |
| 6,017,328 A | 1/2000 | Fischell et al. | |
| D422,356 S | 4/2000 | Marano et al. | |
| 6,056,718 A | 5/2000 | Funderburk et al. | |
| 6,074,371 A | 6/2000 | Fischell | |
| 6,086,575 A | 7/2000 | Mejslov | |
| 6,093,172 A | 7/2000 | Funderburk et al. | |
| 6,123,690 A | 9/2000 | Mejslov | |
| 6,290,688 B1 | 9/2001 | Lopez et al. | |
| 6,293,925 B1 | 9/2001 | Safabash et al. | |
| 6,302,866 B1 | 10/2001 | Marggi | |
| 6,355,021 B1 * | 3/2002 | Nielsen et al. | 604/263 |
| 6,371,943 B1 | 4/2002 | Racz et al. | |
| 6,461,329 B1 | 10/2002 | Van Antwerp et al. | |
| 6,475,196 B1 | 11/2002 | Vachon | |
| 6,517,517 B1 | 2/2003 | Farrugia et al. | |
| 6,520,938 B1 | 2/2003 | Funderburk et al. | |
| 6,529,776 B1 | 3/2003 | Leonard et al. | |
| 6,572,586 B1 | 6/2003 | Wojcik | |
| 6,579,267 B2 | 6/2003 | Lynch et al. | |
| 6,607,509 B2 | 8/2003 | Bobroff et al. | |
| 6,685,674 B2 * | 2/2004 | Douglas et al. | 604/167.05 |
| 6,736,797 B1 | 5/2004 | Larsen et al. | |
| 6,830,562 B2 | 12/2004 | Mogensen et al. | |
| 6,877,713 B1 | 4/2005 | Gray et al. | |
| 6,878,137 B2 | 4/2005 | Benchetrit | |
| 6,923,791 B2 * | 8/2005 | Douglas | 604/167.05 |
| 6,926,694 B2 | 8/2005 | Marano-Ford et al. | |
| 6,939,330 B1 | 9/2005 | McConnell-Montalvo et al. | |
| 6,991,619 B2 | 1/2006 | Marano-Ford et al. | |
| 6,991,620 B2 | 1/2006 | Marano-Ford et al. | |
| 6,997,907 B2 | 2/2006 | Safabash et al. | |
| 7,022,108 B2 | 4/2006 | Marano-Ford et al. | |
| 7,052,483 B2 | 5/2006 | Wojcik | |
| 7,128,730 B2 | 10/2006 | Marano-Ford et al. | |
| 7,207,974 B2 | 4/2007 | Safabash et al. | |
| 7,211,068 B2 * | 5/2007 | Douglas | 604/167.05 |
| 2002/0045867 A1 | 4/2002 | Nielsen et al. | |
| 2002/0095138 A1 | 7/2002 | Lynch et al. | |
| 2002/0123740 A1 | 9/2002 | Flaherty et al. | |
| 2002/0161332 A1 | 10/2002 | Ramey | |
| 2002/0173769 A1 | 11/2002 | Gray et al. | |
| 2003/0060781 A1 | 3/2003 | Mogensen et al. | |
| 2003/0109829 A1 | 6/2003 | Mogensen et al. | |
| 2003/0125669 A1 | 7/2003 | Safabash et al. | |
| 2003/0130619 A1 | 7/2003 | Safabash et al. | |
| 2003/0158520 A1 | 8/2003 | Safabash et al. | |
| 2003/0176852 A1 | 9/2003 | Lynch et al. | |
| 2003/0199823 A1 | 10/2003 | Bobroff et al. | |
| 2003/0216686 A1 | 11/2003 | Lynch et al. | |
| 2003/0225373 A1 | 12/2003 | Bobroff et al. | |
| 2004/0002682 A1 | 1/2004 | Kovelman et al. | |
| 2004/0044306 A1 | 3/2004 | Lynch et al. | |
| 2004/0133164 A1 | 7/2004 | Funderburk et al. | |
| 2004/0138620 A1 | 7/2004 | Douglas et al. | |
| 2004/0143216 A1 | 7/2004 | Douglas et al. | |
| 2004/0158207 A1 | 8/2004 | Hunn et al. | |
| 2004/0204687 A1 | 10/2004 | Mogensen et al. | |
| 2004/0254433 A1 | 12/2004 | Bandis et al. | |
| 2005/0020972 A1 * | 1/2005 | Horisberger et al. | 604/93.01 |
| 2005/0035014 A1 | 2/2005 | Cane | |
| 2005/0043687 A1 | 2/2005 | Mogensen et al. | |
| 2005/0101910 A1 * | 5/2005 | Bowman et al. | 604/93.01 |
| 2005/0101912 A1 | 5/2005 | Faust et al. | |
| 2005/0101932 A1 | 5/2005 | Cote et al. | |
| 2005/0101933 A1 | 5/2005 | Marrs et al. | |
| 2005/0107743 A1 * | 5/2005 | Fangrow, Jr. | 604/164.01 |
| 2005/0113761 A1 | 5/2005 | Faust et al. | |
| 2005/0124936 A1 | 6/2005 | Mogensen et al. | |
| 2005/0215979 A1 | 9/2005 | Kornerup et al. | |
| 2005/0283114 A1 | 12/2005 | Bersina et al. | |
| 2006/0036214 A1 | 2/2006 | Mogensen et al. | |
| 2006/0095003 A1 | 5/2006 | Marano-Ford et al. | |
| 2006/0129090 A1 * | 6/2006 | Moberg et al. | 604/93.01 |
| 2006/0129123 A1 | 6/2006 | Wojcik | |
| 2006/0161108 A1 | 7/2006 | Mogensen et al. | |
| 2006/0211990 A1 | 9/2006 | Fangrow | |
| 2006/0211991 A1 | 9/2006 | Fangrow | |
| 2006/0217659 A1 | 9/2006 | Patton | |
| 2006/0224119 A1 | 10/2006 | Fangrow | |
| 2006/0229559 A1 | 10/2006 | Marano-Ford et al. | |
| 2006/0229560 A1 | 10/2006 | Marano-Ford et al. | |
| 2006/0270990 A1 | 11/2006 | Fangrow | |
| 2006/0276760 A1 | 12/2006 | Fangrow | |
| 2007/0021729 A1 | 1/2007 | Mogensen et al. | |
| 2007/0049870 A1 | 3/2007 | Gray et al. | |
| 2007/0088254 A1 | 4/2007 | Destefano | |
| 2007/0093754 A1 | 4/2007 | Mogensen et al. | |

FOREIGN PATENT DOCUMENTS

| | | |
|---|---|---|
| EP | 0268480 | 5/1989 |
| EP | 0363953 | 4/1990 |
| EP | 0451040 | 10/1991 |
| EP | 0864333 A2 | 9/1998 |

| | | |
|---|---|---|
| WO | WO88/03816 | 6/1988 |
| WO | WO97/37713 | 10/1997 |
| WO | WO98/41384 | 9/1998 |
| WO | WO98/58693 | 12/1998 |
| WO | WO 99/33504 A1 | 7/1999 |
| WO | WO99/44655 | 9/1999 |
| WO | WO 00/25852 | 5/2000 |
| WO | WO 02/070037 A2 | 9/2002 |
| WO | WO 02/081012 A2 | 10/2002 |
| WO | WO 02/081012 A3 | 10/2002 |
| WO | WO 02/083206 A2 | 10/2002 |
| WO | WO 02/083206 A3 | 10/2002 |
| WO | WO 02/094352 A2 | 11/2002 |
| WO | WO 02/100457 A2 | 12/2002 |
| WO | WO 03/022348 A1 | 3/2003 |
| WO | WO 03/026726 A1 | 4/2003 |
| WO | WO 03/068305 A1 | 8/2003 |

OTHER PUBLICATIONS

Medtronic Minimed—History; htt://www.minimed.com/about/history.html; Jun. 5, 2006.
U.S. Appl. No. 11/417,660, filed May 3, 2006.
U.S. Appl. No. 11/417,503, filed May 3, 2006.
U.S. Appl. No. 11/417,613, filed May 3, 2006.
U.S. Appl. No. 10/715,985, Filed May 3, 2006.
U.S. Appl. No. 11/418,725, Filed May 3, 2006.
U.S. Appl. No. 11/417,707, filed May 3, 2006.
U.S. Appl. No. 11/417,699, filed May 3, 2006.
U.S. Appl. No. 11/418,494, filed May 3, 2006.
U.S. Appl. No. 11/417,488, filed May 3, 2006.
U.S. Appl. No. 11/417,660, filed May 3, 2006.
U.S. Appl. No. 11/417,503, filed May 3, 2006.
U.S. Appl. No. 11/417,613, filed May 3, 2006.

* cited by examiner

INFUSION SET

RELATED APPLICATIONS

This application is a continuation of U.S. patent application Ser. No. 10/715,985, filed Nov. 18, 2003 which is incorporated in its entirety by reference herein.

BACKGROUND OF THE INVENTION

1. Field of the Invention

The invention relates in general to the field of infusion sets and more particularly to infusion sets with removable injection needles.

2. Description of the Related Art

Subcutaneous injection is a standard method for the delivery of medication into a patient's body. To facilitate frequent or continuous subcutaneous injection of medication, subcutaneous injection ports are often used. Such injection ports extend through the skin and may remain in place for several days. Currently, a major application of such injection ports is to provide continuous delivery of medication, such as insulin, from portable pumps carried with the patient. When used with a portable pump, the injection port is typically connected to the pump via a fluid line. Another application of subcutaneous injection ports is to permit multiple injections of medication into a patient without the need to repuncture the patient's skin. In this application, medication is injected from a standard medical implement, such as a syringe, through a soft elastomer septum into the injection port which delivers the medication subcutaneously.

Subcutaneous injection ports generally require a sharp, rigid needle to pierce the patient's skin when initially attached to the patient. However, if the needle were left in place through the skin to provide medication delivery, after one or two days the needle would become uncomfortable to the patient. To solve this problem, infusion sets with removable needles and soft plastic cannula to be placed inside the body of a patient have been developed. However, these sets have many disadvantages. There remains a need for an improved infusion set that is less bulky, less susceptible to contamination, more comfortable to a user, and easier to use.

SUMMARY

One embodiment of the present invention provides an infusion set comprising a base member, an introducer cap, and an infusion cap. The base member preferably comprises and a port on a first side thereof, and a soft cannula extending from a second side of the base member. The port is configured to be in fluid communication with the cannula. The port also comprises a septum adapted to seal the port against unwanted fluid flow. The introducer cap is adapted to be mounted to the base member and has a needle adapted to extend through the septum and said soft cannula in an assembled position. The infusion cap comprises a lumen adapted to receive an elongate flexible tube. The infusion cap also comprises a hard cannula adapted to be inserted through the septum and to place said soft cannula in fluid communication with said lumen.

The base member is preferably circular, and the port preferably comprises a cylindrical portion extending from a first side of the base member. The introducer cap preferably comprises a hollow cylindrical portion extending from the second side of the introducer cap and located coaxially with the introducer needle. The infusion cap preferably comprises a hollow cylindrical portion extending from the second side of the infusion cap and located coaxially with the hard cannula. The first side of the infusion cap preferably is dome-shaped, and the infusion cap is preferably adapted to be rotatable relative to the base member when the infusion cap and the base member are assembled.

The base is preferably surrounded by a rim adapted to engage and retain an external component. A cannula extends downward from a first side of said base; and an adhesive layer is secured to the first side of the base. The adhesive layer includes a second side with an adhesive. A substantially cylindrical port extends upward from a second side of said base. The port comprises a septum configured to have a fluid pathway therethrough. The fluid pathway is preferably formed by a slit extending though the septum, but alternatively the fluid pathway can be created by puncturing the septum with a needle or other object. In a method of using an embodiment of the infusion set described herein, the base member is prepared for adhesion to a patient's skin, and the needle and the cannula are inserted through the patient's skin. The introducer cap is disconnected and the needle is withdrawn from the base member. The infusion cap is then assembled on the base member such that the cannula of the infusion cap is in fluid communication with the base cannula, and the infusion cap is rotatable relative to the base member.

BRIEF DESCRIPTION OF DRAWINGS

Having thus summarized the general nature of the invention, certain preferred embodiments and modifications thereof will become apparent to those skilled in the art from the detailed description herein having reference to the figures that follow, of which.

DETAILED DESCRIPTION OF PREFERRED EMBODIMENTS

An infusion set having desirable features and advantages will now be described with reference to the attached figures.

Although the following description is provided in the context of an infusion set for use with an insulin pump, the skilled artisan will recognize that the features of the present infusion set can provide advantages in other applications as well.

Figure 13:
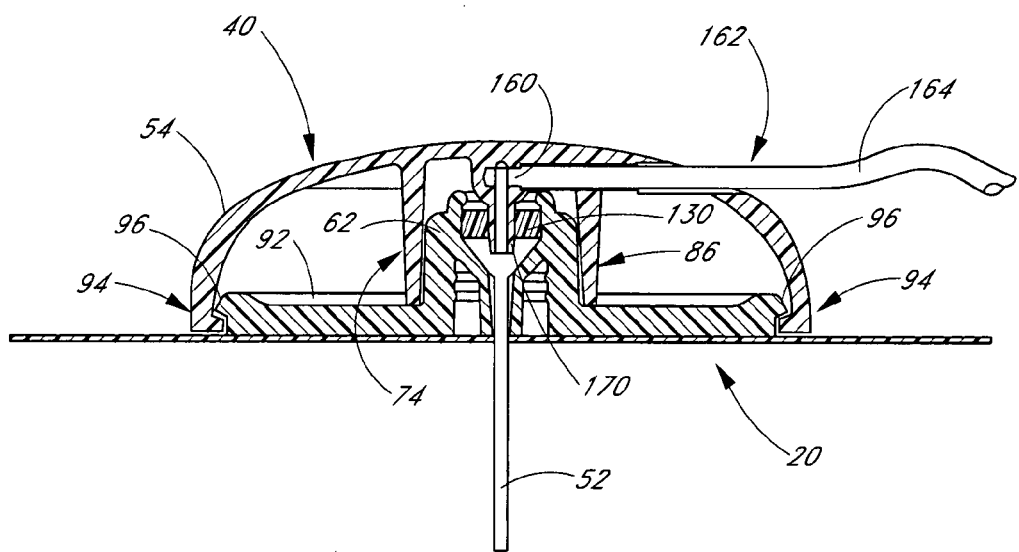
FIG. 13 is a cross-sectional view of the assembly of FIG. 12 taken through line 13-13.

The infusion set illustrated in FIGS. 1-14 and described herein generally comprises a base assembly 20 adapted to removably receive an introducer assembly 30 and an infusion assembly 40 (See FIG. 13).

Figure 1:
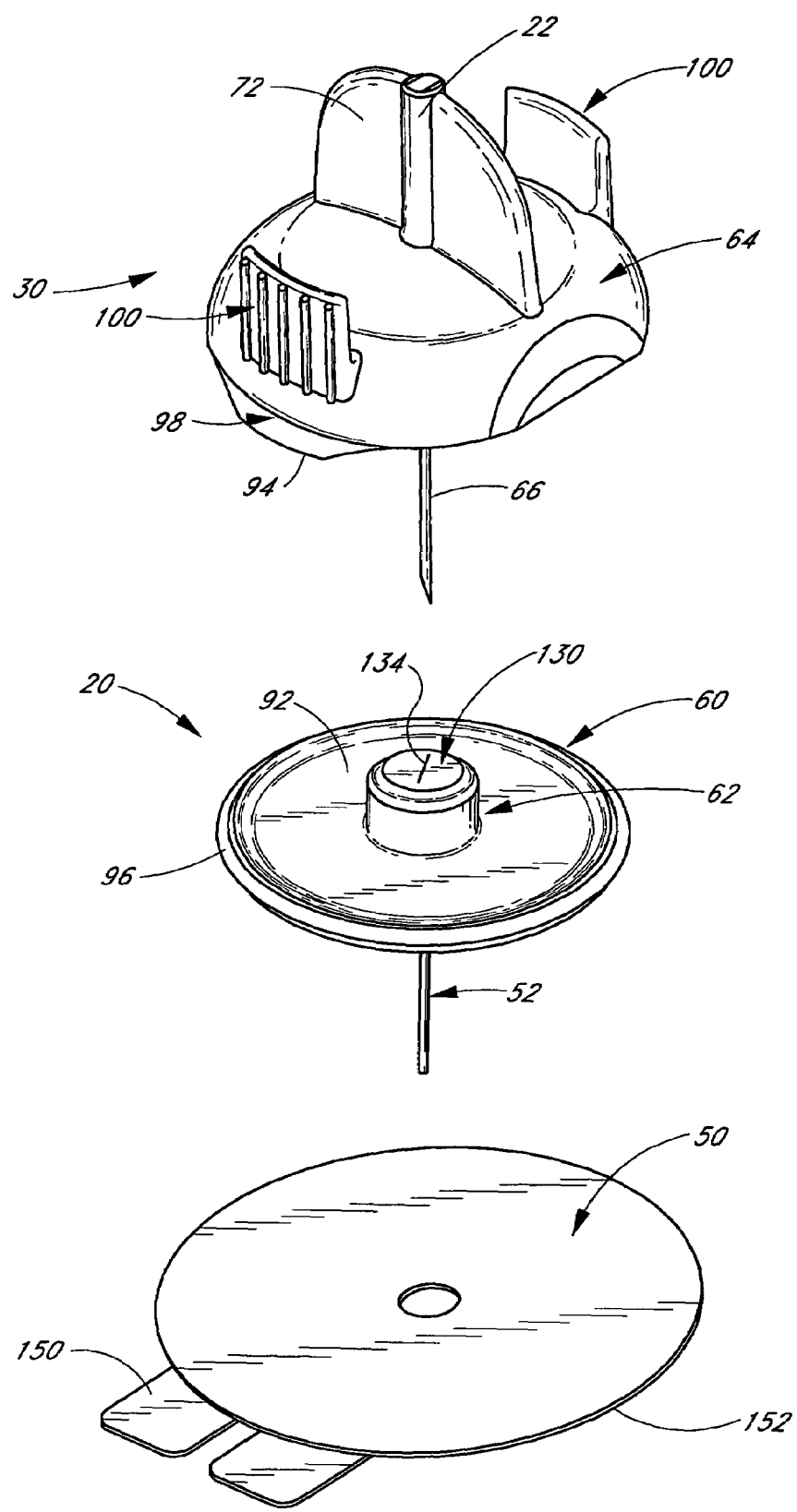
FIG. 1 is a perspective exploded view of an infusion set introducer assembly and base assembly having desired features and advantages.

FIG. 1 illustrates an exploded view of components of the base assembly 20 and the introducer assembly 30. The base assembly 20 is generally configured to be secured to a patient's skin by an adhesive layer 50 to maintain a soft cannula 52 within a patient and to allow an infusion cap 54 (see FIGS. 10-14) to be mounted to the base assembly 20 for delivering a fluid through the cannula 52 and into a patient's body. The base assembly 20 preferably comprises a base member 60 with a soft cannula 52 extending from a first side of the base member 60, a port 62 extending from a second side of the base member 60, and an adhesive layer 50 securable to the second side of the base member 60.

The introducer assembly 30 is generally configured to be removably engageable with the base assembly 20 to facilitate introduction of the soft cannula 52 through a patient's skin to a desired depth in the patient's sub-dermal fatty tissue.

FIGS. 1-4 illustrate embodiments of an introducer assembly 30 comprising an introducer cap 64 and an introducer needle 66 extending downward from the cap 64. In the illustrated embodiment, the introducer cap 64 is generally dome-shaped, and has a handle portion 72, a port-engaging portion 74, a base-engaging portion 76, and release grips 100.

As illustrated, the handle portion 72 generally includes a flange with a needle-holding section 22 extending through a central portion of the flange 72. In one embodiment, the introducer cap 64 is formed with a needle-holding section 22 comprising a lumen into which an introducer needle 66 can be subsequently inserted and secured. Alternatively, the introducer needle 66 can be molded into the material of the introducer cap 64 by any of a variety of over-molding processes available to the skilled artisan. According to one embodiment, the needle-receiving section 22 extends partially into the cavity 84 of the port-engaging portion 74 to provide additional length along which the needle 66 will be supported. The supported length of the needle (i.e. the length of the needle held within the needle-holding lumen 22) can vary as needed for needles of various lengths. For example, in the case of a needle with an overall length of about 1", a needle-receiving section preferably has a length of between about ³⁄₁₆" and about ⁵⁄₁₆".

Introducer needles can be provided in a variety of sizes as needed for a particular cannula or application. For example, needles can be provided with lengths from about 0.5" to about 2" or more. In further alternative embodiments, needles outside of these ranges can also be used as needed. Additionally, an introducer needle can be solid, or may have a hollow inner lumen as desired.

The handle section 72 of the introducer cap 64 is illustrated as comprising a substantially planar section extending upward from the dome-shaped cap 64. The handle section 72 preferably has a substantially large surface area such that a patient or caregiver can easily grasp the introducer cap 64 for assembly with the base member 60 and for insertion of the needle 66 into the patient. For example, as shown, the handle section can extend across a substantial portion of the diameter of the introducer cap. The handle section 72 can also extend upwards from the dome of the cap by about 0.2" to about 1". In one preferred embodiment, the handle section 72 extends about ½" above the top of the introducer cap 64. The skilled artisan will recognize that the handle portion 72 can be otherwise shaped and sized as desired. Alternatively, the introducer cap 30 can be held by the release grips 100 or any other convenient portion during insertion of the needle as will be further described below.

Figure 2:
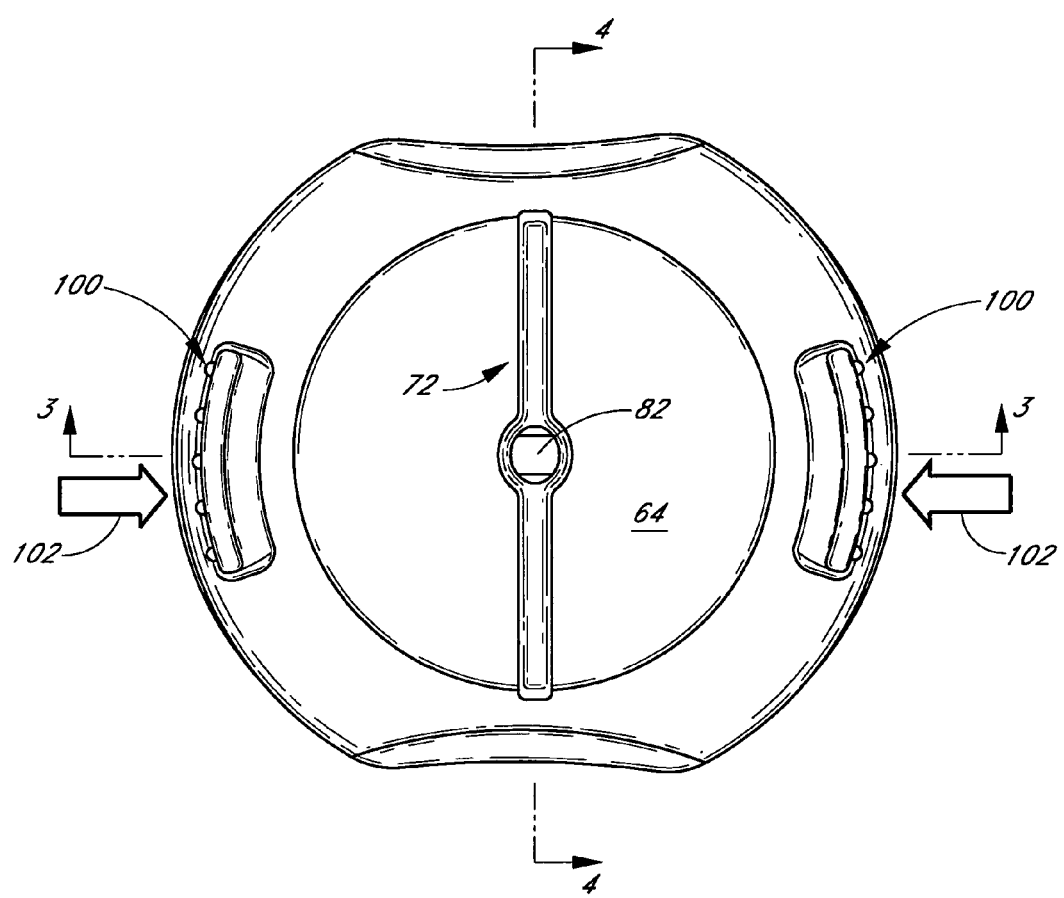
FIG. 2 is a top view of the introducer cap of FIG. 1.

As illustrated in FIG. 2, the port-engaging portion 74 preferably comprises a cylindrical section configured to closely surround the port 62 of the base portion 60 in an assembled position. The tubular wall 86 of the port-engaging portion 74 is generally configured to contact the top surface 92 of the base member 60 as will be further described below. A close fit between the port 62 and the tubular wall 86 of the port-engaging portion 74 of the introducer cap 64 advantageously provides a minimum of movement of the base member 60 relative to the introducer cap 64 during introduction of the needle 66 and catheter 52 into a patient.

Figure 6:
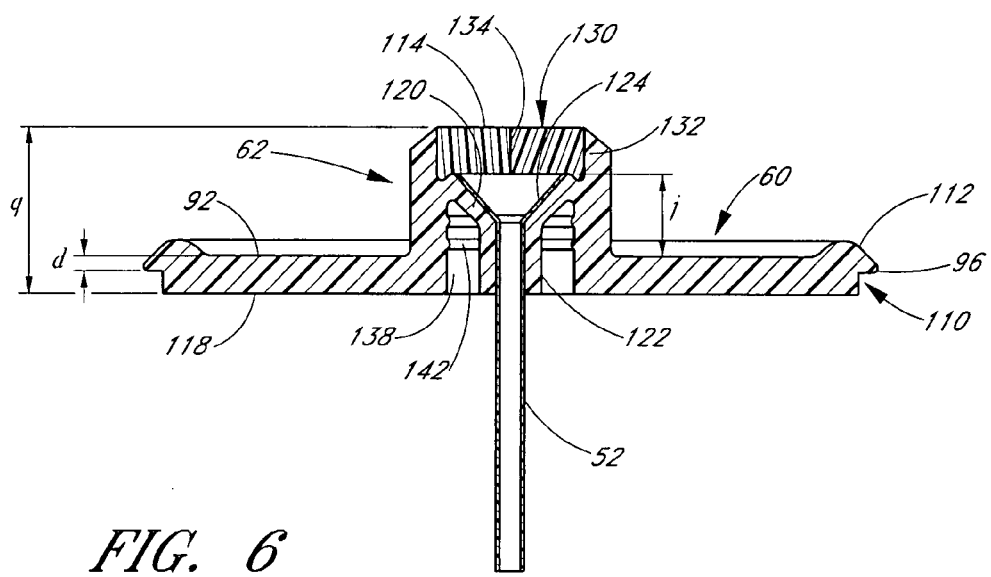
FIG. 6 is a cross-sectional view of the base member of FIG. 4.

In the illustrated embodiment, the base-engaging portion 76 of the introducer cap 64 generally comprises a pair of wings 98 extending downward from the cap. The wings 98 preferably include barbed feet 94 adapted to engage a rim 96 of the base member 60 (FIG. 6). The barbed feet 94 are generally configured to secure the introducer cap to the base member disc 60. The height 'h' between the top of the barbed feet 94 and the bottom of the tubular wall 86 of the port-engaging portion 74 is generally selected to correspond to dimensions of the base member 60 in order to provide a secure fit between the assemblies 20 and 30 as will be further described below. In an alternative embodiment, the barbed feet 94 can be omitted, and the introducer cap can be held in an operative position relative to the base assembly 20 by other means. For example, the port 62 and the port-engaging portion 74 can alternatively be threaded such that the introducer cap can screw onto the base member.

In the illustrated embodiment, the introducer cap 64 is generally circular as viewed from above (see FIG. 2). As shown in FIG. 2, a pair of release grips 100 are provided on opposite sides of the circular cap 64 in the area of the barbed fee 94 so as to allow the introducer cap 64 to be released from engagement with the base member by the application of a force at the arrows 102, preferably by pinching the release grips 100 between the thumb and middle finger. In the embodiments illustrated in FIGS. 2-4 and 8, the release grips 100 comprise vertically extending portions which can be integrally formed with the dome-shaped portion of the introducer cap 64. Alternatively, the vertically extending portions can be separate sections which can be made separately from the introducer cap and secured thereto by any appropriate method. In operation, application of a force at the arrows 102 will create a bending moment at the intersection of the vertically extending portion and the done-shaped cap. This bending moment will cause the wing sections 98 of the introducer cap 64 to bend radially outwards, thereby releasing the barbed feet 94 from engagement with the base member 60.

In alternative embodiments, the release grips 100 can include convex protrusions, concave recesses, or other shapes to allow the shape of the introducer cap to be deformed in order to facilitate removal of the introducer cap 64 from the base member 60. The illustrated release grips 100 advantageously allow the user to grasp the introducer cap 30 with his or her fingers without simultaneously grasping the rim 96 of the base member 60, making it easier to release the introducer cap 64 from the base member 60. Alternatively, a separate tool can also be used to grip an introducer cap 64 and/or an infusion cap 54 during assembly or disassembly of a cap with the base member 60.

The introducer cap 64 is preferably injection molded from a plastic material suitable for use in medical applications. In one embodiment, the introducer cap 64 is made of a biocompatible ABS, and has a wall thickness 't' of about 0.030"+/−0.005". In alternative embodiments, the introducer cap 64 can be made of other biocompatible materials such as polycarbonate in any appropriate size as desired.

Figure 3:
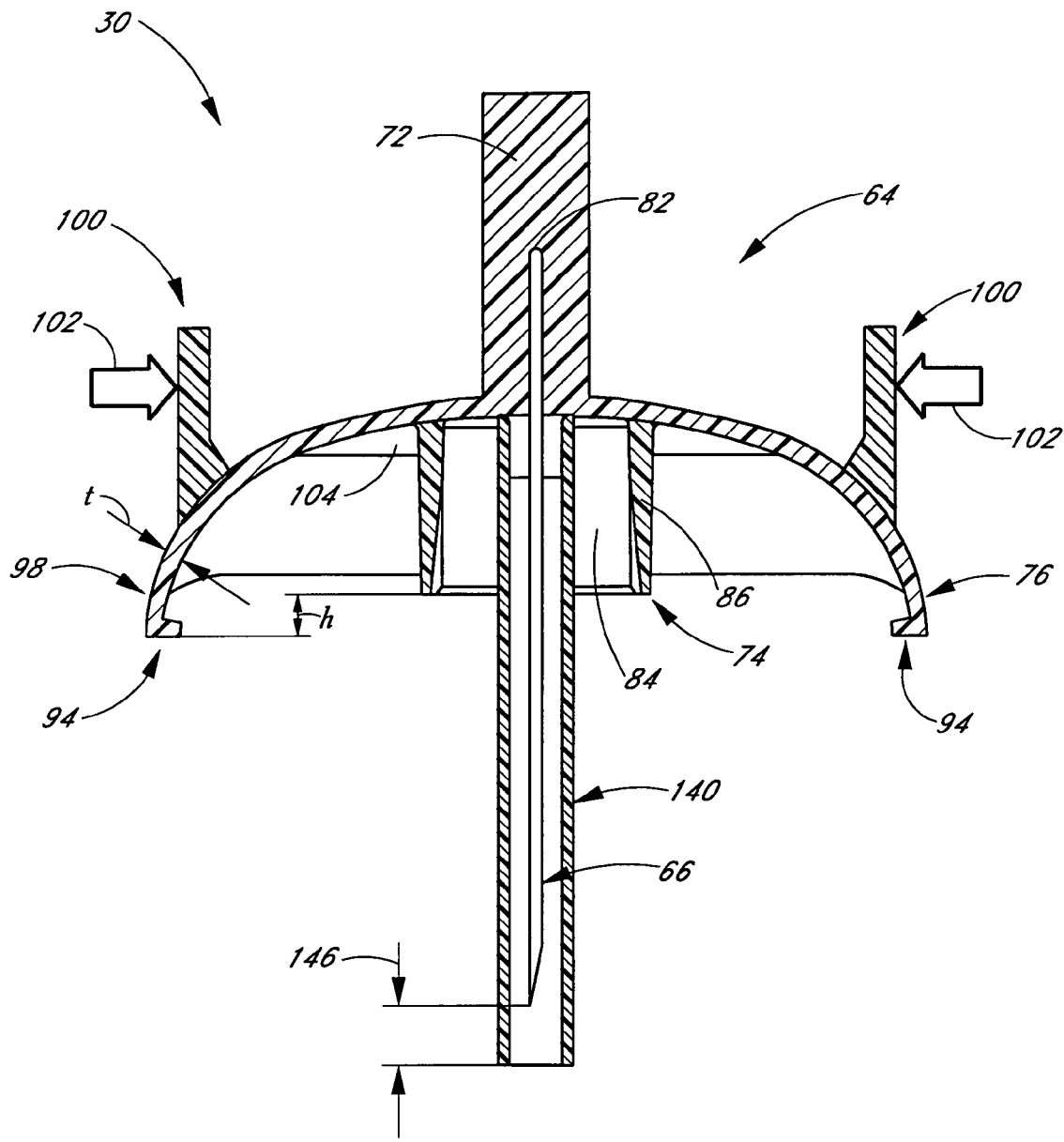
FIG. 3 is a cross-sectional view of the introducer cap of FIG. 1, taken through line 3-3.

As shown in FIG. 3, the introducer cap 64 can also include ribs 104 extending radially from the tubular wall 86 of the port-engaging portion 74. Ribs 104 can be provided in any size and number as desired in order to provide additional rigidity to the joint between the tubular wall and the body of the introducer cap.

Embodiments of the base assembly 20 will now be described with reference to FIGS. 1, 5 and 6. In the illustrated embodiments, the base assembly 20 comprises a base member 60 with a port 62 extending upward therefrom and a soft cannula 52 extending downward from the disc 60. In the illustrated embodiments, the base member 60 is shown as being a substantially circular disc; however, in alternative embodiments, the disc can have other shapes such as an ellipse, polygon, etc. A circular base member 60 as shown provides the advantage of allowing an introducer cap 64 and/or an infusion cap 54 attached thereto to be rotatable about the central axis of the base member 60.

The illustrated base member 60 comprises a rim 96 surrounding the disc-shaped base member 60. The rim 96 is generally configured to receive the barbed feet of an introducer cap 64 and/or an infusion cap 54 to retain the cap member (64 or 54) on the base member 60. As seen in FIG. 6, the rim 96 of the base member 60 can include a notched portion 110 to provide clearance for the barbed feet 94. The rim 96 can also be provided with a sloped edge 112 for facilitating assembly of the cap members 54 and 64 with the base member 60 as the cap is pressed axially downward onto the base member 60 as will be further described below.

With particular reference to FIG. 6, one embodiment of the base member 60 is adapted to have a substantially low profile. For example, in some embodiment, the overall height, 'q' can be between about 0.15" and about 0.25". In one preferred embodiment, the overall height 'q' of the base member 60 is about 0.20".

According to one embodiment, the distance d between the bottom surface of the rim 96 and the top surface 92 of the base member 60 is selected to correspond to the height 'h' between the top edge of the barbed feet 94 and the bottom edge of the tubular wall 86 of the port-engaging portion of the introducer cap 64 (as discussed above with reference to FIG. 3) and the infusion cap 54 (as further discussed below with reference to FIG. 11). In one embodiment, the dimensions 'd' and 'h' are substantially the same, thereby providing a substantially rigid connection between a cap (64 or 54) and the base member 60. Alternatively, the dimension 'h' can be made larger than the dimension 'd' in order to provide a looser connection between a cap (64 or 54) and the base member 60.

Certain advantages arise from loose or tight connections between the base member 60 and a cap member (64 or 54). For example, a tight connection between the base member 60 and the introducer cap 64 will assist in control of the needle 66 during insertion of the needle 66 and the soft cannula 52 through the patient's skin. On the other hand, a loose but secure connection between the base member and the infusion cap 54 will allow the infusion cap 54 to rotate and move about the base member without transmitting substantial torsional stress to the base member 60 and the patient.

As illustrated in FIG. 6, the base member 60 comprises a fluid pathway extending from the top 114 of the port 62 through the soft cannula 52 extending from the bottom surface 118 of the base member 60. The central portion of the fluid pathway preferably comprises a substantially funnel-shaped section 120 with a tubular lower section 122. According to one embodiment, a funnel-shaped insert 124 can be provided to line the interior surface of the funnel-shaped section 120. The insert 124 is preferably made of a rigid material, such as a metal, to protect the wall of the funnel-shaped section 120 during insertion of the introducer needle 66 (FIGS. 1 and 3). The insert 124 prevents the wall of the funnel-shaped section 120 from scoring and/or causing fragments of the wall to break away and enter the infusion stream.

The soft cannula 52 extending from the base member 60 can comprise any material recognized as being suitable for use in fluid-carrying lumens implantable within a patient's body. Infusion sets can be offered with soft cannulas having a variety of lengths to accommodate differences in the desired depth to which the cannula extends within a patient. As will be understood by the skilled artisan, in many embodiments the soft cannula 52 preferably extends into a subcutaneous fat layer of a patient. Thus, cannulas of various length are helpful in allowing a variety of different patients with more or less subcutaneous fat to use the present infusion set. For example, soft cannulas can be produced in lengths from about ¼" to about 2". Depending upon the intended use, soft cannulas with lengths outside of this range may also be employed.

Figure 5:
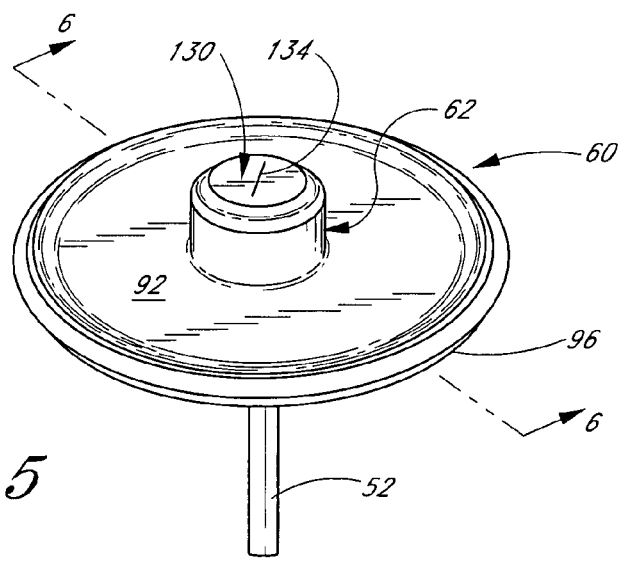
FIG. 5 is a perspective view of the base member of FIG. 1.

FIGS. 1, 5 and 6 illustrate embodiments in which the cannula 52 extends from the bottom surface 118 of the base member 60 at a substantially right angle. In alternative embodiments, the cannula 52 can be configured to extend from the base member at an angle substantially less than 90°.

In alternative embodiments, the soft cannula 52 could be replaced by a substantially hard cannula or hypodermic needle as may be desired. Such a hard cannula or needle could also be provided at any angle relative to the bottom surface 118 of the base member 60 as desired.

In one embodiment, the soft cannula 52 can be secured to the funnel-shaped insert 124, and the cannula-funnel assembly can be inserted into the funnel-shaped section 120 of the base member 60. In an alternative embodiment, the soft cannula 52 can be secured directly to the base member to extend from the bottom surface 118 of the base member 60 at an inner or outer surface of the tubular lower section 122 of the funnel-shaped portion as desired.

As shown in FIGS. 1, 5 and 6, the port 62 extending from the base member 60 preferably comprises a self-sealing septum 130 positioned in the cavity 132 above the funnel-shaped section 120 of the port 62. The septum 130 is preferably positioned at or near the top of the port 62 so as to present a readily accessible surface for swabbing with antiseptic to maintain the septum 130 free of bacteria and other debris. The positioning of the septum above the funnel-shaped section 120 helps maintain the funnel-shaped section 120 sterile. In the illustrated embodiment, the septum 130 preferably comprises a slit 134 forming a fluid pathway through the septum 130. Although the illustrated slit 134 is in the shape of a straight line, in alternative embodiments, the slit 134 can be circular, cross-shaped, or otherwise shaped to provide a sealable fluid pathway through the septum 130. In further alternative embodiments, a pre-formed slit 134 can be omitted, and the septum 130 can be punctured with a needle or other sharp object to create a fluid pathway through the septum 130.

In order to create a self-sealing fluid pathway, the septum 130 is generally made of a substantially resilient material biased toward a sealed position. In one embodiment, the septum 130 is made of a molded disc of silicon, polyurethane or other appropriate material which can be secured to the port 62. The securing of the septum 130 to the port 62 can be accomplished by any suitable adhesive, bonding or other securement process such as heat sealing, sonic welding, etc. In alternative embodiments a suitably resilient material such as silicone, polyurethane, or other suitable elastomeric material can be molded into the cavity 132 at the top of the port 62 (see FIG. 6). In still further embodiments, the septum 130 can be replaced by any of a variety of mechanical check-valves or other seals configured to provide a re-sealable fluid pathway. In another embodiment, the septum 130 and the body of the base member 60 can both be integrally formed from the same substantially resilient material.

Figure 8:
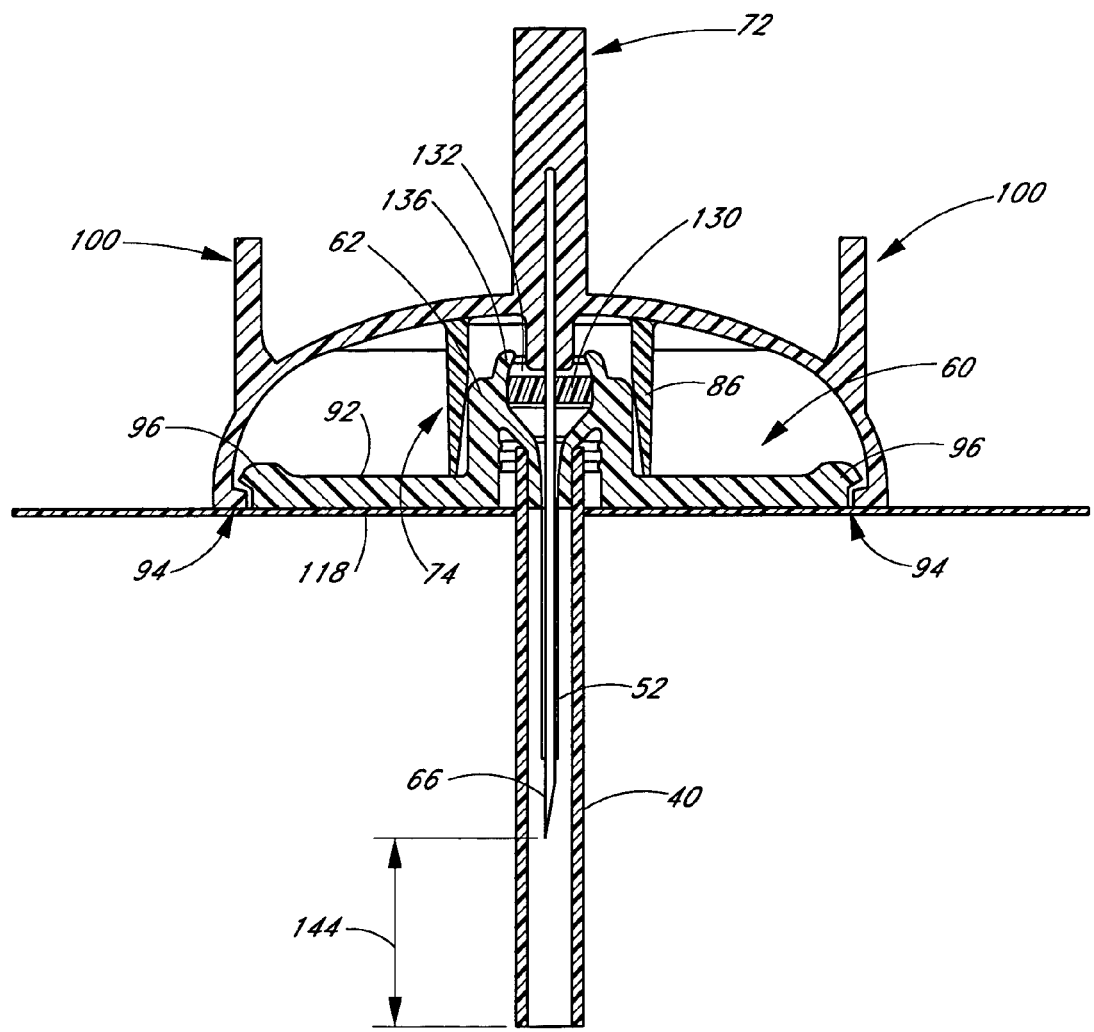
FIG. 8 is a cross-sectional view of the assembly of FIG. 7 taken through line 8-8.

According to one embodiment, as illustrated for example in FIG. 8, the septum 130 is a molded disc of a substantially resilient material that is retained in the port 62 by heat staking. As shown, a portion of a port wall 136 is provided that extends above the septum 130 and surrounds the cavity 132 in which the septum 130 is located. The port wall 136 is heat staked by slightly heating the material of the wall 136 to a temperature below its melting temperature, but sufficiently high to soften the material of the wall. Once the port wall 136 material has been softened, it can be deformed radially inward slightly so as to trap the septum 130 in the cavity 132 of the port 62. The heat staking procedure can be performed uniformly around the circumference of the port, or at intervals around the wall 136. The skilled artisan will recognize that alternative methods can also be used for securing the septum within the cavity 132, such as bonding, welding, etc. as described above.

Figure 4:
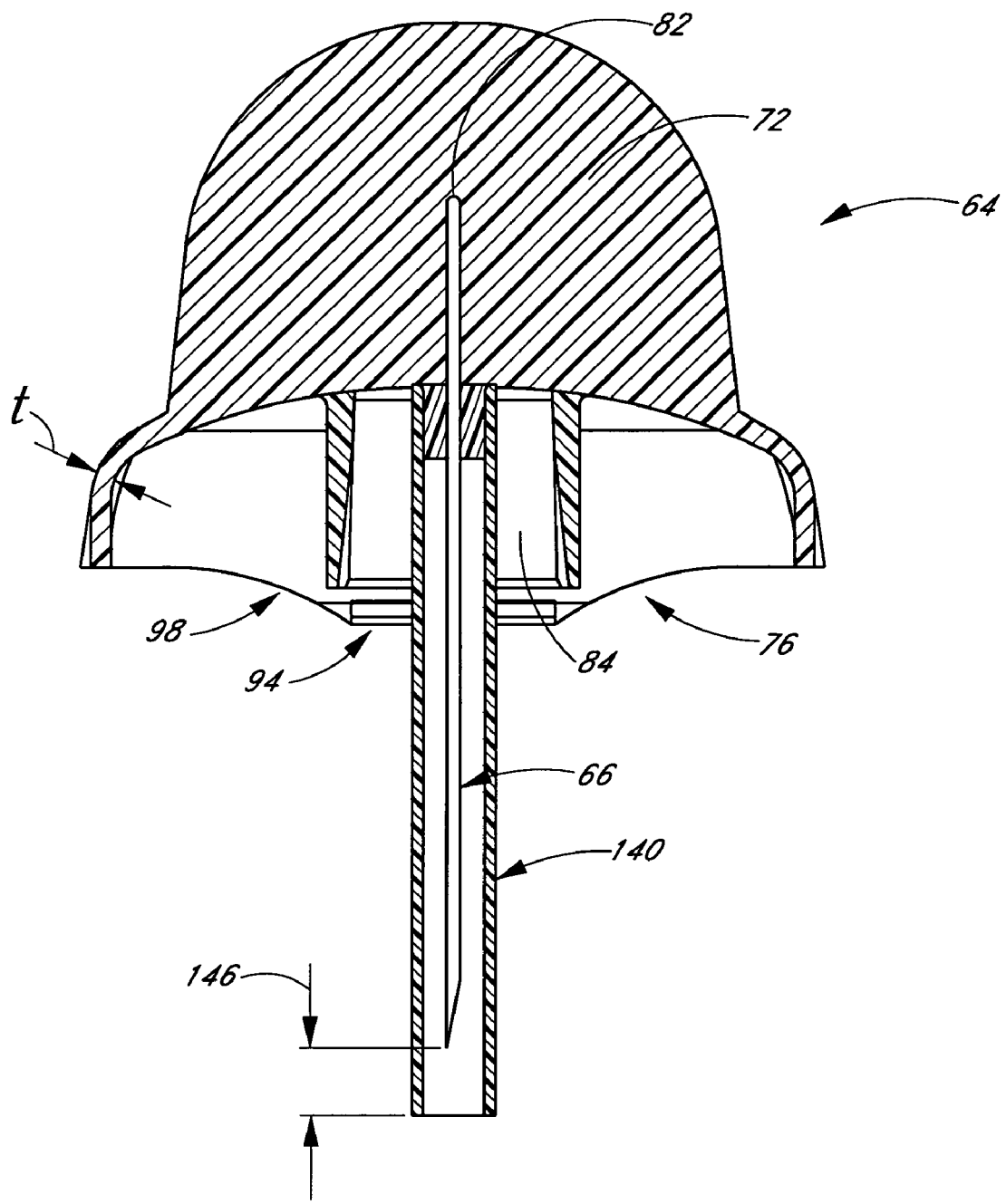
FIG. 4 is a cross-sectional view of the introducer cap of FIG. 1, taken through line 4-4.

As shown in FIG. 6, the tubular lower portion 122 of the funnel-shaped section 120 is surrounded by an annular space 138 configured to allow a needle guard 140 to be affixed to the funnel-shaped section 120. (see FIGS. 8 and 9). In the embodiments illustrated in FIGS. 7 and 8, the needle guard 140 comprises a section of tubing of sufficient length and rigidity that the guard 140 will not expose the sharpened needle tip. The needle guard 140 can comprise any suitable material and/or design as desired. For example, in one embodiment, the needle guard 140 comprises a section of vinyl tubing which extends 144 about ⅛" to about ½" beyond the needle tip in the assembled position shown in FIG. 8. In alternative embodiments, the annular space 138 can be omitted and the needle guard 140 can be retained over the needle 66 by some other means, such as by a tighter friction-fit around the needle 66 or by providing a needle guard as part of the packaging for the infusion assembly. In some embodiments, as illustrated in FIGS. 3 and 4, the needle guard 140 can be configured to be attached directly to the introducer cap 64 in order to extend at least a distance 146 of between about 1/16" and about ⅛" or more beyond the needle tip. In an alternative embodiment, a needle guard can be provided to attach to the barbed feet 94 of the introducer cap 64 after the introducer cap 64 has been removed from the base member 60.

If desired, the annular space 138 of the base member 60 can be provided with annular rings 142 to aid in release of the base member from a mold half during an injection molding process. As will be clear to the skilled artisan, it is often desirable that an injection molded part remain temporarily retained in one of the halves of an injection mold until the mold half is moved to a location over a drop bucket, at which time the part can be ejected from the mold by ejector pins. In the absence of the annular rings 142, an injection molded base member 60 may prematurely fall out of the mold. It should be noted that the base member 60 need not be made by injection molding, and could be made by any number of other suitable processes in which case, the annular rings 142 might be excluded.

According to one embodiment, an adhesive layer 50 such as that illustrated in FIG. 1 can be secured to the bottom surface of the base member 60. The adhesive layer 50 is generally configured to allow the base member 60 to adhere to a patient's skin as will be further described below. The adhesive layer 50 is typically provided with a backing layer 150 to protect the adhesive side 152 of the adhesive layer 50 from dirt, dust and other contaminants that may reduce the ability of the adhesive side 152 to securely adhere to a patient's skin and may increase the risk of infection at the injection site. The adhesive layer 50 can be secured to the bottom surface 118 of the base member 60 by any suitable bonding substance or process. For example, the adhesive layer can be adhered to the base member with a glue or other bonding agent. Alternatively the adhesive layer 50 can be bonded to the base member 60 by heat sealing, sonic welding, or any other suitable process. Alternatively, the function of adhering the base member 60 to a patient's skin may be accomplished by other means known to those of skill in the art.

Figure 7:
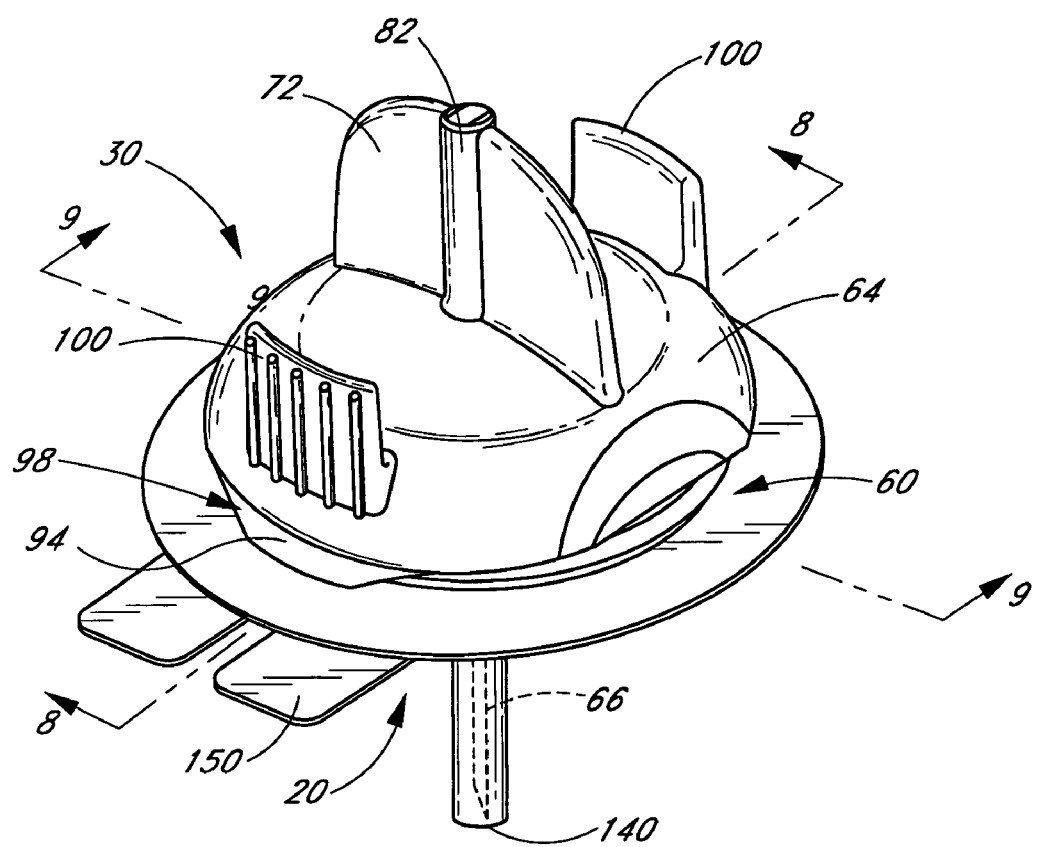
FIG. 7 is a perspective view of an assembled introducer and base member.
Figure 9:
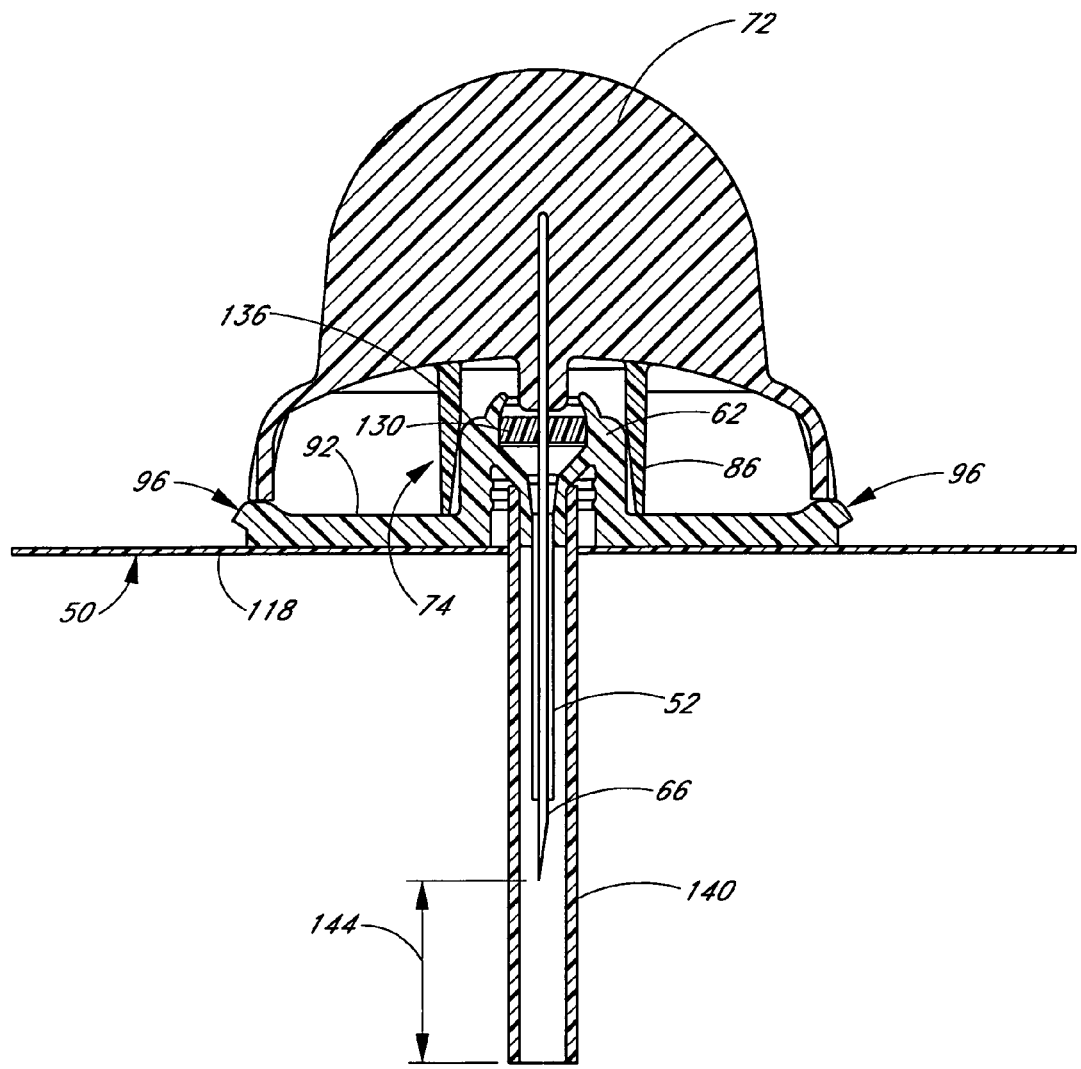
FIG. 9 is a cross-sectional view of the assembly of FIG. 7 taken through line 9-9.
Figure 10:
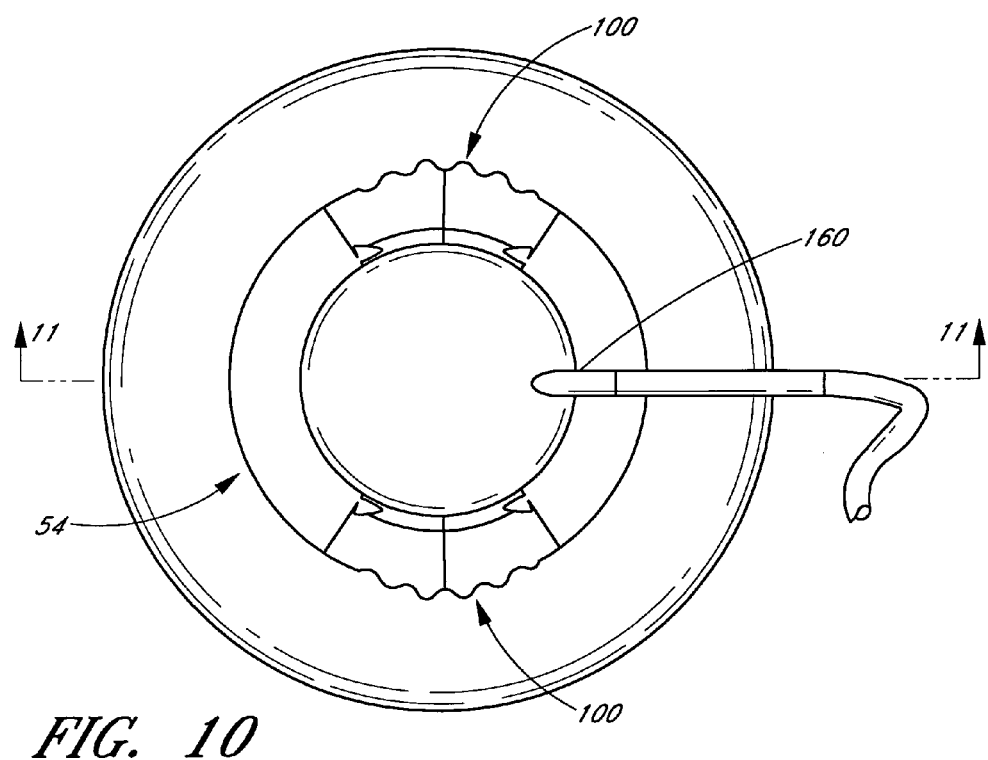
FIG. 10 is a top view of an infusion cap having desired features and advantages.

FIGS. 7-9 illustrate one embodiment of an introducer assembly 30 attached to a base assembly 20. As shown, the introducer cap 64 is preferably attached to the base member 60 by the engagement of the barbed feet 94 with the rim 96 of the base member 60. By removably engaging the introducer cap to the base member 60, the needle 66 is temporarily secured within the cannula 52 to provide a rigid puncturing surface during the process of inserting the cannula 52 into the patient's body. If the introducer cap 64 or needle 66 were not engaged with the base member 60, then the introducer cap 64 and base member 60 could separate or become misaligned during insertion into the patient, possibly entailing repeated puncturing, and causing unnecessary pain and discomfort to the patient. In the illustrated embodiment, the engagement of the introducer cap 64 and the base member 60 allow these components to be pressed together against the patient, preferably with a single, rapid motion. The cylindrical wall 86 of the port-engaging portion 74 also preferably engages the upper surface 92 of the base member 60.

The port-engaging portion 74 of the introducer cap 64 is preferably adapted to surround the port 62 of the base member 60. This provides for a close fit between the introducer cap 64 and the base member. This close fit can aid in preventing the base member from rocking or performing other unwanted movement relative to the introducer cap 64. These same advantages can also be beneficial in the context of the infusion cap 54 as will be further described below. In one embodiment, the inner diameter of the port-engaging portion 74 is about 0.025" to about 0.1" larger than the port 62 of the base member 60. Depending upon the desired application, in alternative embodiments, the inner diameter may be outside of this range.

With reference to FIGS. 10-14, embodiments of infusion assemblies 40 adapted to be mounted to the base member 60 will now be described. As illustrated, an infusion cap 54 can be configured to attach to a base member 60 in a similar manner to that of the introducer caps 64 discussed above.

Figure 11:
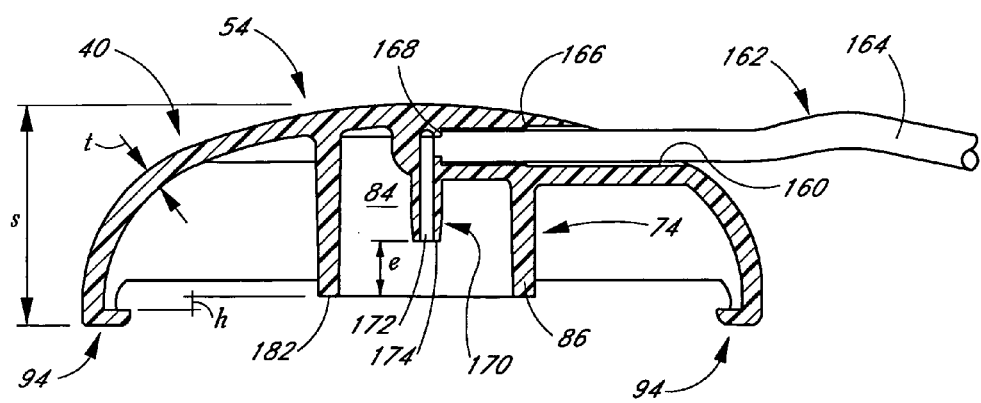
FIG. 11 is a cross-sectional view of the infusion cap of FIG. 10 taken through line 11-11.
Figure 12:
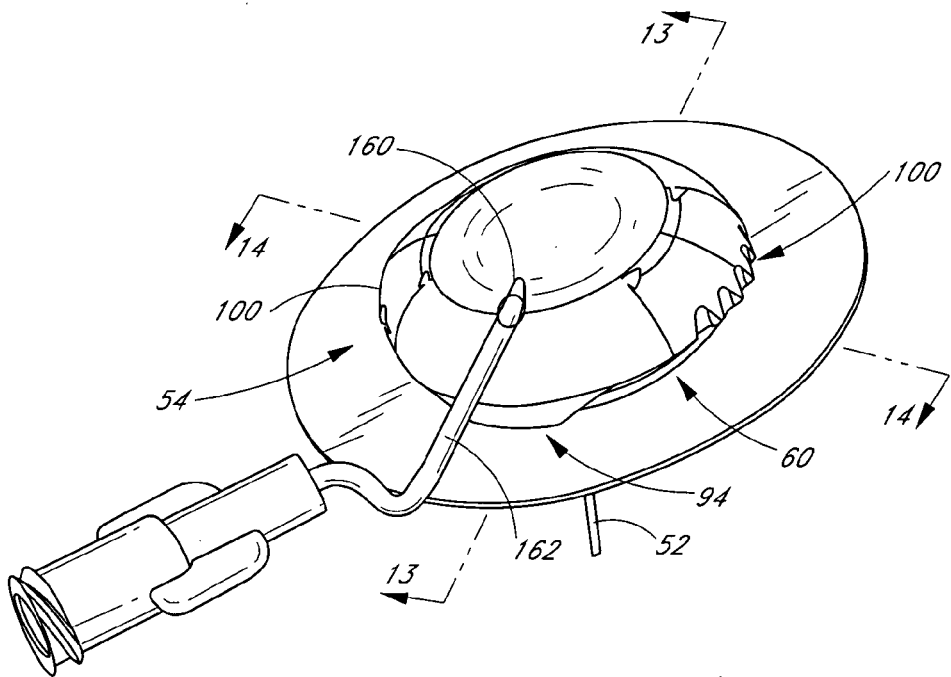
FIG. 12 is a perspective view of an assembly of an infusion cap and a base member.

With reference to FIG. 11, one embodiment of the infusion cap 54 is adapted to have a substantially low profile. For example, in some embodiment, the overall height, 's' can be between about 0.300" and about 0.400". In one preferred embodiment, the overall height 's' of the infusion cap 54 is about 0.335".

In one embodiment, an infusion cap 54 comprises a tube-receiving lumen 160. The tube-receiving lumen 160 is generally configured to accept a section of flexible tubing 162 with an internal lumen 164 as shown in FIG. 11. The tube-receiving lumen 160 can comprise any appropriate transverse cross-section (e.g. as viewed in the axial direction) as desired, but will typically have an axial cross-section corresponding to an axial cross-section of the selected tube 162.

The tube 162 typically comprises a circular cross-section with a diameter of between about 0.030" and about 0.10". The tube can be any material suitable for use in transmitting fluids in medical applications. Typically the tube will be made of polyethylene or medical grade polyvinyl chloride, although other materials can alternatively be used. The end of the tube 162 that is opposite from the infusion cap can be provided with a connector for joining the tube in fluid communication with the output of a pump or other fluid source. For example, in one embodiment, the opposite end of the tube 162 comprises a Luer lock connector. Other connectors can alternatively be used as will be understood by the skilled artisan in view of the present disclosure.

The tube 162 can be secured to the infusion cap 54 by any suitable process or mechanism as desired. For example, in the illustrated embodiment, the tube-receiving lumen 160 tapers in diameter from the outer end 166 to the inner end 168. This taper provides for a tight press-fit, allowing the tube to be retained by friction between the inner wall of the tube-receiving lumen 160 and the outer wall of the tube 162. If desired, the tube 162 can be further secured in the tube-receiving lumen by adhesives, sonic welding, heat sealing, or any other suitable process.

Figure 14:
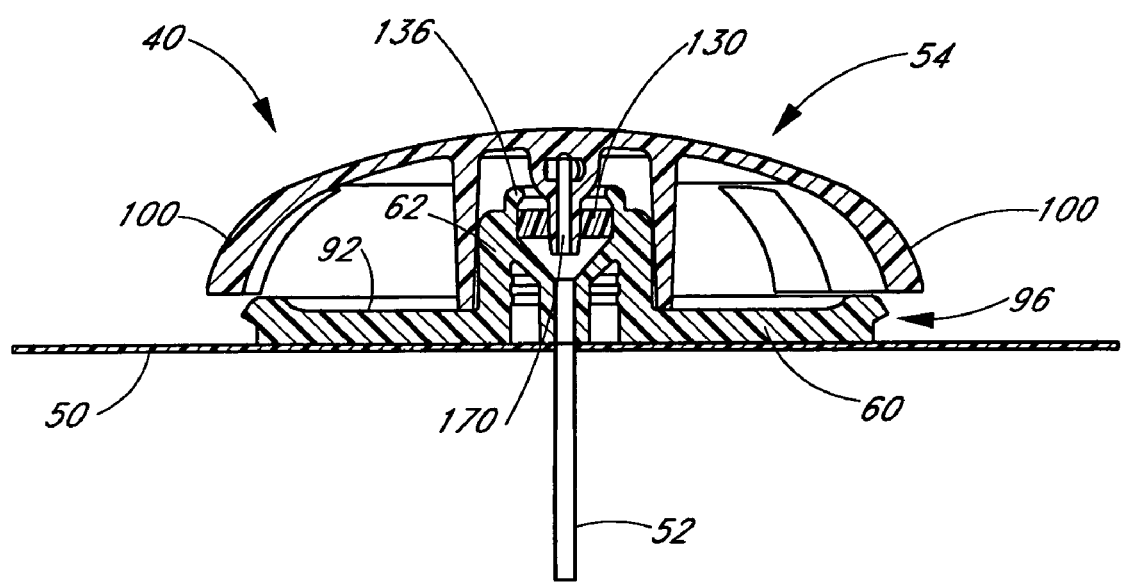
FIG. 14 is a cross-sectional view of the assembly of FIG. 12 taken through line 14-14.

As can be seen in FIGS. 11, 13 and 14, the infusion cap 54 can further comprise a hard cannula 170 with a lumen 172 configured to be in fluid communication with the tube 162. The hard cannula 170 can be integrally molded as part of the infusion cap 54, or it can be subsequently attached by any suitable process. The inner diameter of the hard cannula lumen 172 will typically be selected to allow a sufficient fluid flow rate therethrough. For example, in some embodiments, the lumen 172 has an internal diameter of between about 0.01" and about 0.03", and in one embodiment, the lumen 172 has an internal diameter of about 0.02". Other diameters outside of these ranges can alternatively be used as desired.

In the embodiment of FIG. 9, the hard cannula 170 is surrounded by a cylindrical wall 86 to protect the cannula 170 from contact with a user's fingers, or other objects that might contaminate the sterility of the lumen. The hard cannula 170 can be positioned within the cylindrical wall 86 such that the cannula is substantially co-axial with the cylinder wall 86, thereby providing for automatic alignment of the cannula with the exact center of the septum 130 as the cylinder wall 86 engages the port 62. As described with reference to the introducer cap 64 above, the cylindrical wall 86 of the infusion cap 54 is preferably sized and configured to provide a substantially close fit with the port 62 of the base member 60. Providing a close fit advantageously assists in alignment of the hard cannula 170 with the port. The close fit also advantageously causes any forces applied to the infusion cap 54, such as the cap being bumped or the tube 162 being pulled, will be applied at the intersection of the port and the port-engaging portion 74 rather than at the barbed feet (which could cause the infusion cap to become disconnected from the base member 60).

The hard cannula 170 is generally configured to extend through at least a portion of the septum 130 when the infusion cap 54 and base member 60 are assembled. Thus, the hard cannula 170 is typically dimensioned such that it extends into the port-engaging portion 74 a sufficient distance that when the wall of the port-engaging portion contacts the top surface 92 of the base member 60, the hard cannula 170 will extend through at least a portion of the septum 130. Thus, the dimension 'j' between the outlet 174 of the hard cannula 170 and the bottom edge 182 of the port-engaging portion 74 is preferably less than the dimension 'j' between the top surface 92 of the base member and the bottom of the cavity 132 in the port 62 (see FIG. 5). In alternative embodiments, the dimension 'e' can be equal to or greater than the dimension 'j' if it is desirable that the hard cannula 170 extend only partially through the septum 130, for example. In one preferred embodiment, as illustrated in FIG. 11, the hard cannula 170 extends completely through the septum 130.

The hard cannula 170 also preferably has sufficient column strength to be inserted through the septum 130 (or other sealing member). Thus, the hard cannula 170 is typically made of a rigid material such as PVC, PET, nylon, stainless steel, or other material suitable for use in medical applications and having sufficient rigidity.

Similarly to the introducer cap 64, the infusion cap 54 also preferably comprises release grips 100 which can be compressed to release the cap from engagement with the base member 60. In the embodiment illustrated in FIGS. 10, the release grips 100 are shown as scalloped convex segments located at about 90° to the wings 98 and barbed feet 94. The release grips 100 can be engaged by a user's fingers to release the cap 54 or 64 from engagement with the base member 60. By pinching the release grips 100, the circular shape of the cap 64 is deformed into an elliptical shape with the barbed feet 94 along the major axis of the ellipse. Thus, pinching the cap 64 at the release grips 100 causes the barbed feet to move radially outwards and away from the edges of the base member 60, thereby releasing the cap 64 from the base member 60. In alternative embodiments, the release grips 100 of the introducer cap 64 and/or the release grips 100 of the infusion cap 54 can comprise smooth convex sections, concave sections, or any of a variety of other shapes.

Methods of using the infusion set embodiments described above will now be described with continued reference to FIGS. 1-11. In preparation for introduction of the infusion set into a patient, the base assembly 20 and the introducer assembly 30 will typically be assembled as shown in FIGS. 6 and 7. In some embodiments, the base assembly 20 and the introducer assembly 30 can be provided to an end user in a pre-assembled condition. Alternatively, in other embodiments, the parts can be provided separately for assembly by an end user.

According to one embodiment, a patient will follow these steps in order to introduce the soft cannula 52 and connect the infusion set. The patient can remove the needle guard 140 from the position shown in FIG. 7 by gripping the needle guard 140 and pulling it axially away from the introducer cap 64, thereby exposing the introducer needle 66 and the soft cannula 52 extending from the underside 118 of the base member 60.

The backing layer 150 can then be removed from the adhesive layer 50, thereby exposing the "sticky" side of the adhesive layer to be adhered to the patient's skin. While gripping the introducer cap 64 in any desirable manner, or using any suitable tool, the introducer needle 66 and soft cannula 52 are rapidly pressed against and inserted through the patient's skin and into the patient's sub-dermal tissue until the adhesive layer 50 contacts the patient's skin and adheres thereto. The adhesive layer 50 is preferably substantially free from folds or 'bubbles,' thereby forming a close, secure attachment.

Once the needle 66 and soft cannula 52 have been inserted to the desired depth, the introducer cap 64 can be removed from the base member 60 and from the patient. In order to remove the introducer cap 64 from the base member 60, the release grips 100 can be engaged by a user's fingers and compressed, thereby deforming the circular cap and causing the barbed feet 94 to be released from engagement with the rim 96 of the base member 60. In alternative embodiments, the release grips 100 can be compressed by a supplemental tool. In further alternative embodiments, the introducer cap 64 can be configured such that release grips are otherwise manipulated (e.g. twisted, spread apart, etc.) in order to remove the introducer cap 64 from the base member. In still further embodiments, the barbed feet 94 may be omitted, as discussed above, or replaced with a suitable alternative structure, thereby allowing a user to merely pull outward on the introducer cap 64 to remove the needle 66.

Once the introducer cap 64 is disengaged from the base member 60, the cap is pulled outward and away from the patient, and the needle 66 is withdrawn from the soft cannula 52. The soft cannula remains within the patient, extending to a desired depth within the patient's sub-dermal tissue and held in place by the base member 60 and the adhesive layer 50. As described above, the septum 130 is generally configured to seal the fluid pathway upon removal of the needle 66, thereby preventing unwanted flow of fluids or contaminants through the cannula 52.

Once the base member 60 and cannula 52 are in place, the infusion cap 54 can be joined to the base member 60, thereby placing the tube lumen 164 of the infusion tube 162 in fluid communication with the soft cannula 52. As the user assembles the infusion cap 54 with the base member 60, the port-engaging portion 74 will surround the port 62, thereby aligning the hard cannula 170 of the infusion cap 54 with the slit 134 in the septum 130. As mentioned previously, the slit can be pre-formed, or a hole can be formed by the needle 66 extending through the septum 130. The automatic alignment of the hard cannula with the septum slit 134 allows for simple assembly and diminished risk of misalignment. This is particularly advantageous to diabetic patients who often have deteriorating eyesight.

The infusion cap 54 can be pressed against the base member until the barbed feet 94 "snap" into engagement with the rim 96 of the base member. In one embodiment, the infusion cap 54 can be configured to create an audible "snap" sound when it is pressed onto the base member 60 to enable a user to audibly and/or tactilely verify the complete engagement of the infusion cap 54 on the base member 60.

There are many circumstances, such as when the patient bathes, sleeps, plays sports, etc., when it is desirable to disconnect the infusion set without removing the cannula from the patient's body. When the infusion set is disconnected, the base member is exposed to potential contamination by dust, dirt, bacteria and other contaminants. In addition, the possibility of the base member becoming snagged or pulled by clothing or other objects poses potential problems. As will be clear to the skilled artisan in view of the present disclosure, these issues and others are addressed by the advantageous features of the infusion set embodiments shown and described herein.

The illustrated infusion set provides for repeated disconnection and reconnection of the infusion cap 54 to and from the base member 60. The infusion cap 54 can be removed from the base member 60 by engaging and applying a force to the release grips 100 in order to cause the barbed feet 94 to disengage from the rim 96 of the base member 60. Similarly to the introducer cap 64, the infusion cap 54 can be engaged by a user's fingers or any other appropriate tool or device to facilitate removal of the cap from the base member 60.

The infusion set embodiments described herein provide a single fluid pathway through the base member by allowing the hard cannula 170 of the infusion cap 54 to extend through the same path through the base member as the needle 66 of the introducer cap 64. This arrangement advantageously reduces the number of possible points of contamination within the infusion system. When the infusion cap 54 is removed, the septum 130 will seal the fluid pathway to prevent the unwanted egress of blood, and to prevent particles and unwanted fluids from entering the patient through the cannula 52.

As mentioned above, the base member 60 and cannula 52 can be left in place within a patient for a few days or longer, and in some circumstances, the base member may be left disconnected from the infusion cap for a period of a few hours or more. The illustrated base member 60 has an advantageously low profile, thereby reducing the likelihood of the base member 60 becoming "snagged" on clothing, towels, or other objects when the patient bathes, dresses, etc. The dome-shaped infusion cap of the above embodiments also advantageously covers the entire base member, thereby protecting the base member from contamination by dirt, dust, germs, or other contaminants. The low profile of the base member 60 and the substantially flat top surface of the septum 130 are also advantageously substantially free from cavities or crevices which might hold contaminants. In addition, the low-profile design diminishes the likelihood that a patient will inadvertently bump or jostle the infusion set during use, causing discomfort and/or requiring repositioning or replacement of the infusion set.

Additionally, the position of the septum 130 at a distal surface of the base member relative to the patient's body advantageously provides for simplified cleaning of the septum. As shown and described above, the septum 130 is preferably positioned such that it is flush with the top edge of the port 62. This provides for easy cleaning of the septum 130 and the port 62, such as with a cotton swab and alcohol, or any other cleaning products suitable for use in medical applications.

In other circumstances, it is desirable for the infusion set to have substantial freedom of movement while installed and assembled. For example, once assembled, the embodiment of an infusion set illustrated in FIG. 12 has the advantage that the infusion cap 54 can rotate relative to the base member about an axis perpendicular to the plane of the bottom surface 118 of the base member and extending through the center of the port 62. Such rotatability advantageously allows a patient to move the tube 162 to the front or the back of the patient's body without inducing a twisting moment on the base member 60. Thus, an infusion set having an infusion cap that is capable of rotation about a central axis of a base member while maintaining fluid communication between a pump and a patient's body has the distinct advantage of providing the patient with substantial freedom to position the infusion tube 162 at any radial position relative to the base member.

The end of the tube 162 that is opposite the infusion cap can be connected to a suitable pump or other fluid source either before of after assembly of the infusion cap 54 and base member 60. In alternative embodiments, an infusion system may comprise additional tubes, connectors, or other components between the soft cannula and a fluid source.

In alternative embodiments, the base member 60 shown and described herein can be employed to deliver medicants or other therapeutic fluids to a patient without the use of the other members of the infusion set described herein. For example, a base member such as those described above could be used in combination with a standard hypodermic syringe to deliver a therapeutic fluid to a patient by extending a cannula of the syringe through the septum and injecting the fluid through the soft cannula of the base member and into the patient.

Although certain embodiments and examples have been described herein, it will be understood by those skilled in the art that many aspects of the methods and devices shown and described in the present disclosure may be differently combined and/or modified to form still further embodiments. For example, any one component of the infusion sets shown and described above can be used alone or with other components without departing from the spirit of the present invention. Additionally, it will be recognized that the methods described herein may be practiced in different sequences, and/or with additional devices as desired. Such alternative embodiments and/or uses of the methods and devices described above and obvious modifications and equivalents thereof are intended to be included within the scope of the present invention. Thus, it is intended that the scope of the present invention should not be limited by the particular embodiments described above, but should be determined only by a fair reading of the claims that follow.

What is claimed is:

1. An infusion set comprising:
   a base having upper and lower sides, a base cannula extending downwardly from the lower side, and a port extending upwardly from the upper side, the port being in fluid communication with the base cannula, and the port comprising a septum adapted to substantially seal said port from fluid communication therethrough; and
   an infusion cap comprising:
      an upper side and a lower side, the infusion cap being adapted to be pressed against the upper side of the base and removably attached to the base after disengagement of an introducer cap from the base, the infusion cap being adapted to rotate with respect to the base while engaged;
      an infusion cannula extending downwardly from the lower side of the infusion cap;
      an elongate flexible lumen in fluid communication with the infusion cannula, the infusion cannula being adapted to extend through the septum on the upper side of the base upon engagement of the infusion cap and the base to place the flexible lumen and the infusion cap in fluid communication with the base cannula;
      a guide section on the lower side of the infusion cap in close proximity to the infusion cannula, the guide section being configured to align the infusion cap with the port of the base whereby the infusion cannula is directed toward the septum when the infusion cap is removably coupled to the base, wherein the guide section extends downwardly from the lower side of the infusion cap beyond the infusion cannula, wherein the guide section is substantially cylindrical, wherein the infusion cap comprises at least one retaining member to attach to the base, and wherein the lowest surface of the guide section is upwardly spaced from the lowest surface of the at least one retaining member.

2. The infusion set of claim 1, wherein the septum is pre-slit.

3. The infusion set of claim 1, wherein the guide section surrounds the infusion cannula.

4. The infusion set of claim 1, wherein the guide section and the cannula are substantially co-axial.

5. The infusion set of claim 1, wherein the base further comprises a rim and the at least one retaining member attaches to the rim of the base.

6. The infusion set of claim 5, wherein the retaining member is a foot.

7. The infusion set of claim 5, wherein the infusion cap further comprises at least a second retaining member to attach to the rim of the base.

8. An infusion set comprising:
   a base having upper and lower sides, a base cannula extending downwardly from the lower side, and a port extending upwardly from the upper side, and the port comprising a septum adapted to inhibit fluid communication through the port; and
   an infusion cap comprising:
      an upper side and a lower side, the infusion cap being adapted to be pressed against the upper side of the base and removably coupled to the base, the infusion cap being adapted to rotate with respect to the base while the infusion cap and the base are coupled;
      an infusion cannula extending downwardly from the lower side of the infusion cap, the infusion cannula being adapted to extend through the septum on the upper side of the base upon coupling of the infusion cap and the base to place the infusion cannula in fluid communication with the base cannula;
      a guide section on the lower side of the infusion cap in close proximity to the infusion cannula, the guide section being configured to assist in aligning the infusion cap with the port of the base whereby the infusion cannula is directed toward the septum when the infusion cap is removably coupled to the base wherein the guide section extends downwardly from the lower side of the infusion cap beyond the infusion cannula, wherein the guide section is substantially cylindrical, wherein the infusion cap comprises at least one retaining member to attach to the base, and wherein the lowest surface of the guide section is upwardly spaced from the lowest surface of the at least one retaining member.

9. The infusion set of claim 8, wherein the infusion cap is adapted to be removably coupled to the base after disengagement of an introducer cap from the base.

10. The infusion set of claim 8, wherein the infusion cap further comprises an elongate flexible lumen in fluid communication with the infusion cannula.

11. The infusion set of claim 8, wherein the septum is pre-slit.

12. The infusion set of claim 8, wherein the guide section surrounds the infusion cannula.

13. The infusion set of claim 8, wherein the guide section and the cannula are substantially co-axial.

14. The infusion set of claim 8, wherein the base further comprises a rim and the at least one retaining member attaches to the rim of the base.

15. The infusion set of claim 14, wherein the retaining member is a foot.

16. The infusion set of claim 14, wherein the infusion cap further comprises at least a second retaining member to attach to the rim of the base.

* * * * *

UNITED STATES PATENT AND TRADEMARK OFFICE
CERTIFICATE OF CORRECTION

PATENT NO. : 7,297,138 B2  Page 1 of 1
APPLICATION NO. : 11/417655
DATED : November 20, 2007
INVENTOR(S) : Thomas F. Fangrow It is certified that error appears in the above-identified patent and that said Letters Patent is hereby corrected as shown below:

At page 3, at column 1, line 16, please delete "03/026726" and insert -- 03/026728 --, therefor.
At page 3, at column 2, line 1, please delete "htt://" and insert -- http:// --, therefor.
At column 5, line 46, please delete "d" and insert -- 'd' --, therefor.
At column 7, line 42, after "120" delete ".".
At column 10, line 16, please delete "'j'" and insert -- 'e' --, therefor.
At column 14, line 51 (approx.), in Claim 8, after "base" insert -- , --.

Signed and Sealed this

Fourteenth Day of September, 2010

David J. Kappos
*Director of the United States Patent and Trademark Office*